United States Patent [19]

Love et al.

[11] Patent Number: 4,911,816
[45] Date of Patent: Mar. 27, 1990

[54] PROCESS FOR CONDUCTING ELECTROPHORESIS AND TRANSFER

[75] Inventors: Jack D. Love, Wheaton; Michael T. Elliott, Gaithersburg; Patricia L. Morgan, Hyattsville; Leo G. Woerner, Towson, all of Md.

[73] Assignee: Oncor, Inc., Gaithersburg, Md.

[21] Appl. No.: 298,254

[22] Filed: Jan. 17, 1989

Related U.S. Application Data

[63] Continuation of Ser. No. 77,240, Jul. 24, 1987, abandoned, which is a continuation-in-part of Ser. No. 825,921, Feb. 4, 1986, Pat. No. 4,726,889, and a continuation-in-part of Ser. No. 911,467, Sep. 25, 1986, Pat. No. 4,756,809.

[51] Int. Cl.$^4$ ...................... B01D 57/02; G01N 27/28
[52] U.S. Cl. ............................... 204/299 R; 204/182.8
[58] Field of Search ............ 204/299 R, 182.8, 182.9, 204/180.1

[56] References Cited

U.S. PATENT DOCUMENTS

| | | | |
|---|---|---|---|
| 3,047,489 | 7/1962 | Raymond | 204/182.8 X |
| 3,407,133 | 10/1968 | Oliva et al. | 204/182.8 X |
| 3,494,846 | 2/1970 | Arquemboug | 204/299 R X |
| 3,715,295 | 2/1973 | Tocci | 204/299 R X |
| 3,751,357 | 8/1973 | Rains | 204/299 R |
| 3,873,433 | 3/1975 | Seidel et al. | 204/182.8 |
| 3,888,759 | 8/1988 | Elson et al. | 204/299 R |
| 4,151,065 | 4/1979 | Kaplan et al. | 204/299 R |
| 4,588,491 | 5/1986 | Kreisher et al. | 204/299 R |
| 4,657,655 | 4/1987 | Smoot et al. | 204/299 R |

FOREIGN PATENT DOCUMENTS 8702132 4/1987 World Int. Prop. O. .

OTHER PUBLICATIONS

M. Bittner, et al., "Electrophoretic Transfer of Proteins and Nucleic Acids from Slab Gels to Diazobenzyloxymethyl Cellulose or Nitrocellulose Sheets", Analytical Biochemistry 102, pp. 451–471 (1980).
Bethesda Research Laboratories, Inc., "Catalogue & Reference Guide", Aug. 1983, p. 51.

Primary Examiner—John F. Niebling
Assistant Examiner—John S. Starsiak, Jr.
Attorney, Agent, or Firm—Burns, Doane, Swecker & Mathis

[57] ABSTRACT

An apparatus for carrying out horizontal gel electrophoresis for separation and subsequent vacuum-assisted transportation of macromolecules to a support membrane to facilitate detection. The entire procedure is conducted in one cartridge. A method for conducting electrophoresis and subsequent vacuum assisted transfer using the apparatus of the present invention is also disclosed.

28 Claims, 8 Drawing Sheets

PROCESS FOR CONDUCTING ELECTROPHORESIS AND TRANSFER

CROSS REFERENCE TO RELATED APPLICATIONS

This application is a continuation of application Ser. No. 077,240, filed July 24, 1987, now abandoned, which is a continuation-in-part of our copending applications Ser. No. 825,921, filed Feb. 4, 1986, now U.S. Pat. No. 4,726,889, and Ser. No. 911,467, filed Sept. 25, 1986, now U.S. Pat. No. 4,756,809, entitled Process and Apparatus for Conducting Electrophoresis and Transfer.

FIELD OF THE INVENTION

This invention relates to processes and apparatus for carrying out horizontal gel electrophoresis for separation and subsequent vacuum assisted transportation of macromolecules to a support membrane to facilitate detection.

BACKGROUND OF THE INVENTION

The process known as electrophoresis involves the migration of charged molecules through a suitable retarding medium under the influence of an electric field. Generally, the compounds of higher molecular weight migrate at a slower rate through the medium than do the compounds of lower molecular weight. Devices have been provided previously for carrying out electrophoresis. An example of such a device is U.S. Pat. No. 4,415,418 in which a tray is provided with a raised platform at the center. Removable partitions are placed in the tray at opposite ends of the platform, and a conventional electrophoresis gel is poured over the platform to form a thin layer. When the gel has cooled, the partitions are removed. A comb is provided to form wells across the surface of the gel. Substances that are to be subjected to electrophoresis are delivered into each of the wells, and the tray is at least partially filled with an electrolyte buffer. Electrodes are positioned at each end of the tray and a sufficient voltage difference is applied to the electrodes to cause migration of the molecules of the substance in the wells across the length of the gel, separated according to their molecular weight. After electrophoresis, the gel is removed from the original casting tray, and placed in a dish containing depurination solution. Approximately thirty minutes later this solution is poured out by tipping the dish toward one edge while the gel is held with the fingers. It is important to use great care during this procedure to prevent the gel from breaking because there is no gel support structure and subsequent processing is possible only with an integral gel. A denaturation solution is then added to the dish and incubation is continued for approximately thirty minutes. Again, the solution is carefully poured off. Then neutralization buffer is added and incubation is continued for thirty additional minutes.

In accordance with conventional techniques, transfer of the nucleic acids is accomplished by placing a piece of filter paper, which is as wide as and longer than the gel, on a platform which is suspended above a solution of 10× saturated saline citrate buffer (SSC). The ends of the filter paper are long enough to hang off the ends of the platform and dip into the 10× SSC. Thus, the filter paper acts as a wick to absorb the SSC solution. The gel is removed from the dish and placed on top of the filter paper saturated with 10× SSC. Next, a piece of membrane filter paper which is the same size as the gel is saturated with 10× SSC and placed on top of the gel. The nucleic acids are eventually bound to the membrane filter paper. Another piece of saturated filter paper, the same size as the gel, is placed on top of the membrane. The entire layered unit is then smoothed to remove any air bubbles that may exist between the gel and the filter paper. Finally, a stack of paper towels, the same size as the gel, is positioned on top of the layered unit.

Over a period of about 12 to 16 hours, the 10× SSC solution is drawn up through the gel by capillary action and the nucleic acids are transferred out of the gel into the membrane above. The paper towels absorb the excess buffer and provide the force for capillary action. At the end of the transfer period, the entire layered unit is disassembled and the membrane is removed for hybridization. This technique is described in an article by E. Southern, "Detection of Specific Sequences Among DNA Fragments Separated by Gel Electrophoresis," *J. Mol. Biol.*, 98:503 (1975).

Although the trays such as the one described in U.S. Pat. No. 4,415,418 are convenient for carrying out electrophoresis, they are not suitable for situations where a large number of samples must be tested in a relatively short period of time.

Therefore, the prior art uses a tedious multi-step, multi-apparatus process for preparing nucleic acid fragments for subsequent hybridization. Four steps are generally undertaken to achieve preparation of the sample for hybridization. Electrophoresis was previously described. Depurination removes purine bases from nucleic acids. Denaturation involves separating the strands of nucleic acids and breaks down the depurinated nucleic acids into suitable size to allow eventual transfer of the fragments out of the gel. Transfer involves allowing the fragments to go out of the gel onto the porous membrane.

OBJECTS OF THE INVENTION

It is the principal object of the present invention to provide on apparatus wherein the steps of electrophoresis depurination, denaturation and transfer to a membrane may all be carried out.

It is an object of the present invention to standardize and simplify the electrophoresis and transfer techniques to facilitate applications of molecular biology.

It is a further object of the present invention to provide a process for electrophoresis and transfer which offers considerable time and cost savings.

Yet another object of the present invention is to provide an electrophoretic system wherein a uniform flow rate of buffer solution above and below the gel surface is maintained, even at low flow rates.

Still another object of the present invention is to provide a more efficient method for handling the gel and further processing.

Another object of the present invention is to provide an electrophoretic system including a photoadapter which permits ultraviolet light to be directed onto a membrane and which permits photographs to be taken of the membrane.

SUMMARY OF THE INVENTION

In accordance with the present invention, nucleic acid fragments such as DNA and RNA may be prepared for subsequent hybridization using the process and apparatus of this invention. The process and apparatus are particularly useful for detection of gene rearrangements, restriction fragment polymorphisms and restriction fragment patterns. The process enables rapid screening of nucleic acids from tissue specimens and body fluids for the presence of infectious viruses such as Human Papilloma virus, for typing B-cell and T-cell monoclonal populations, and for screening patients for the development of cancer or other disease states.

In a first embodiment, the apparatus of the present invention permits electrophoresis and transfer to be conducted in a single unit. The unit includes a tray having opposite side walls, opposite end walls and a bottom wall. There is a central platform in the tray, with a vacuum chamber between the platform and the bottom wall. The platform surface is pervious to liquid. A liquid reservoir is provided adjacent each of the end walls and electrophoresis electrodes are mounted in the reservoirs. A conduit is provided for transferring liquid into and out of the tray. The tray may be covered by a lid. The unit is adapted to perform electrophoresis and vacuum transfer without removing the gel from the tray.

A second, embodiment of the invention also permits electrophoresis and transfer to be conducted in a single unit. Like the first embodiment, the unit of the second embodiment includes a tray having opposite side walls, opposite end walls, a bottom wall, a central platform in the tray, a vacuum chamber between the platform and the bottom wall and a platform surface which is pervious to liquid. An electrode for applying an electric field is provided in the tray adjacent the end walls. The platform is located between the electrodes. There is also a conduit for transferring liquid into and out of the tray. The conduit has a port of a size large enough to prevent formation of bubbles in the liquid. Unlike the first embodiment, there is a dam which extends between opposite side walls of the tray at each end of the platform. The dam has a slot along the bottom wall of the tray. The tray may be covered by a lid. The unit is adapted to perform electrophoresis and transfer without removing the gel from the tray.

The process of the present invention is performed by placing the gel on a porous platform in a tray. Samples are deposited in spaced wells in the gel. An electrophoresis buffer is supplied to the tray to cover the gel and the electrodes. An electric potential is applied between the electrodes. After the electrophoresis step, depurination and denaturation are carried out while the gel remains in the tray. In one embodiment, a transfer membrane is inserted manually between the gel and the platform before the electrophoresis step. In an alternative embodiment a transfer membrane is inserted manually between the gel and the platform during the denaturation step, and the liquid is drawn through the porous membrane to cause the displaced samples to be transferred from the gel to the membrane. The membrane is then removed from the tray. Of course, if a conventional apparatus is used for electrophoresis, the tray of this invention can be used for transfer of the fragments from the gel to the membrane by vacuum transfer in accordance with this invention.

DETAILED DESCRIPTION OF THE DRAWINGS

Preferred embodiments of the invention are illustrated in the accompanying drawings, in which.

DETAILED DESCRIPTION

Figure 1:
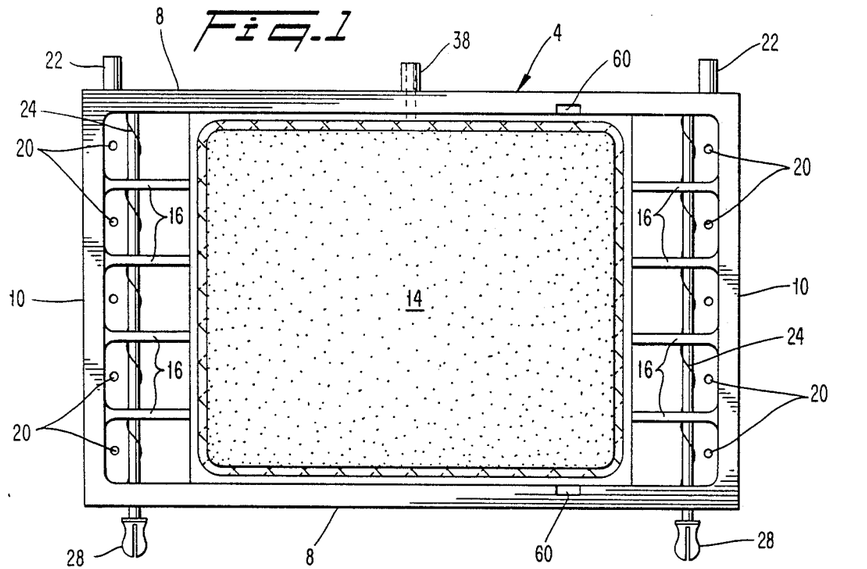
FIG. 1 is a top plan view of the electrophoresis transfer tray of the first embodiment in accordance with this invention, with the lid removed.
Figure 2:
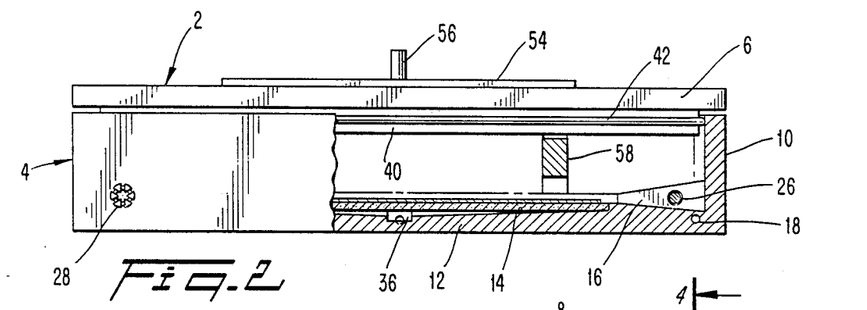
FIG. 2 is a side elevational view of the cartridge of this invention, partially in cross-section.

Referring to FIGS. 1 and 2, a cartridge 2 is used for carrying out the electrophoresis and transfer processes of this invention. The cartridge 2 includes a tray 4 and a lid 6. Tray 4 is preferably composed of polyvinyl chloride or Delrin, a resin which is a registered trademark of E. I. duPont de Nemours & Co. Inc.; however, any material which has good dimensional stability for fabrication is non-electrically conductive and which is chemically compatible with the intended use is suitable. The tray 4 has opposite side walls 8, end walls 10 and a bottom wall 12. A support surface 14 is provided at the center of the tray. The bottom wall 12 adjacent the end walls 10 slopes downwardly, as shown in FIG. 2 away from the support surface 14. A plurality of webs 16 extend inwardly from the end walls 10. The webs facilitate insertion of the gel without tearing. The webs also align the gel thereby assuring proper orientation of the gel in the electric field.

Figure 4:
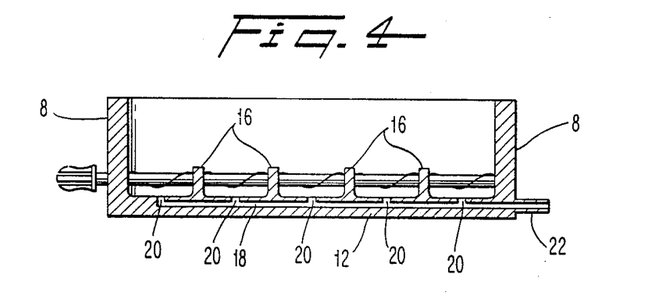
FIG. 4 is a cross-sectional view of the tray along the line 4—4 in FIG. 3.

As shown in FIGS. 2 and 4, a transverse passage 18 is provided in the bottom wall 12 and ports 20 communicate with the passage 18 to allow the circulation of fluid into and out of the tray. A tubing fitting 22 is provided on the side wall 8. An identical passage 18 is provided at the opposite end of the tray (FIG. 1) and has corresponding ports 20 and a tube fitting 22.

Electrodes are provided at each end of the tray. The electrode 24 is in the form of a thin wire, preferably of platinum, which is wrapped on an insulated rod 26. The rod is supported in aligned holes in the webs 16. The electrode 24 extends through the side wall 8 and is connected with an electrical contact element 28 which is adapted to be connected to a source of electric potential.

Figure 5:
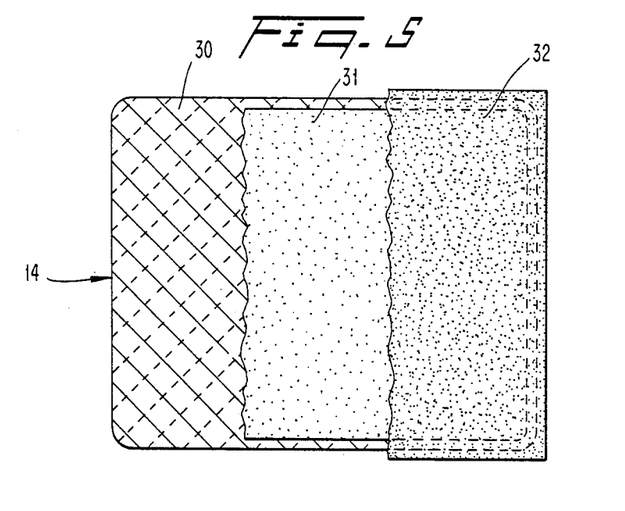
FIG. 5 is a detail view of the plate during the vacuum step showing the membrane and gel superimposed on the plate.
Figure 11:
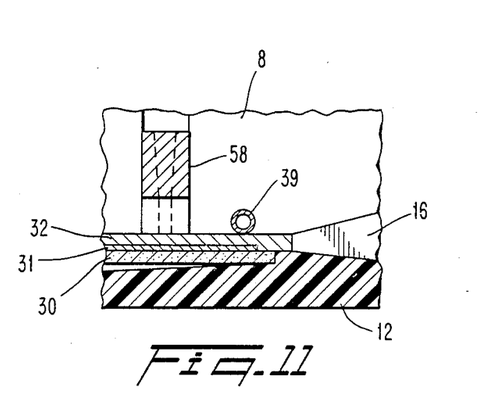
FIG. 11 is a cross-sectional view of the bridge and tray along the line 11—11 in FIG. 9.

The support surface 14 is formed of a porous plate 30 (FIG. 11). Any porous plate is suitable, however, a plate made of a porous polyethylene is preferred. The porous plate should be about 30% to 85% open to sufficiently pull water. As shown in FIG. 5, the plate 30 has parallel score lines on each side which are perpendicular, so that small holes through the plate are formed at the inner section of the score lines. Of course, any suitable porous plate could be substituted for the plate 30. A porous membrane 31 has approximately the same dimensions as the plate 30, so that when it is in place, it substantially covers the plate 30. Membrane 31 must have properties such that it is optimum for binding of vacuum assisted transported DNA fragments. Membrane 31 is preferably comprised of nylon or nitrocellulose such as a nylon membrane comprised of about 02. to 1.2 micron porosity. However, any fluid-permeable membrane which is sufficient to bind nucleic acids would be suitable.

Figure 3:
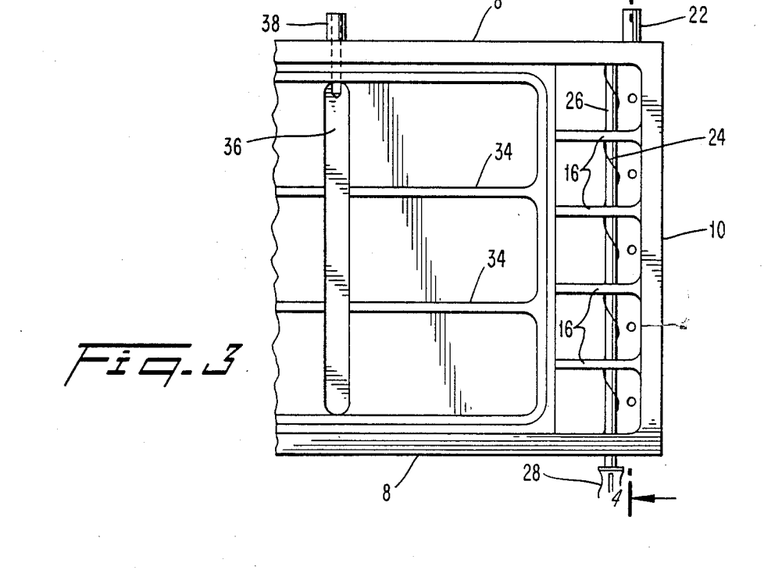
FIG. 3 is a detail top plan view of the tray with the perforated plate removed.

A gel is cast on a separate tray as in conventional practice. The gel can be agarose, polyacrylamide, mixed agarose/polyacrylamide or any other material suitable for the separation of macromolecules in an electric field. Generally, 0.7% w/v agarose is used. The gel 32 is then transferred to the tray 4 where it is superimposed on the plate 30, as shown in FIG. 2. A vacuum chamber is provided beneath the plate 30, as shown in FIGS. 2 and 3. The chamber includes a pair of ridges 34 extending outwardly from a central channel 36. A tubing fitting 38 extends through the side wall 8 and communicates with the channel 36. The fitting 38 is adapted to be connected by tubing to a suitable vacuum pump. The opposite ends of the gel 32, when placed in the tray 4, abut the ends of the webs 16, as shown in FIG. 11. The side edges of the gel 32 are positioned by engagement with the side walls 8 of the tray.

Figure 6:
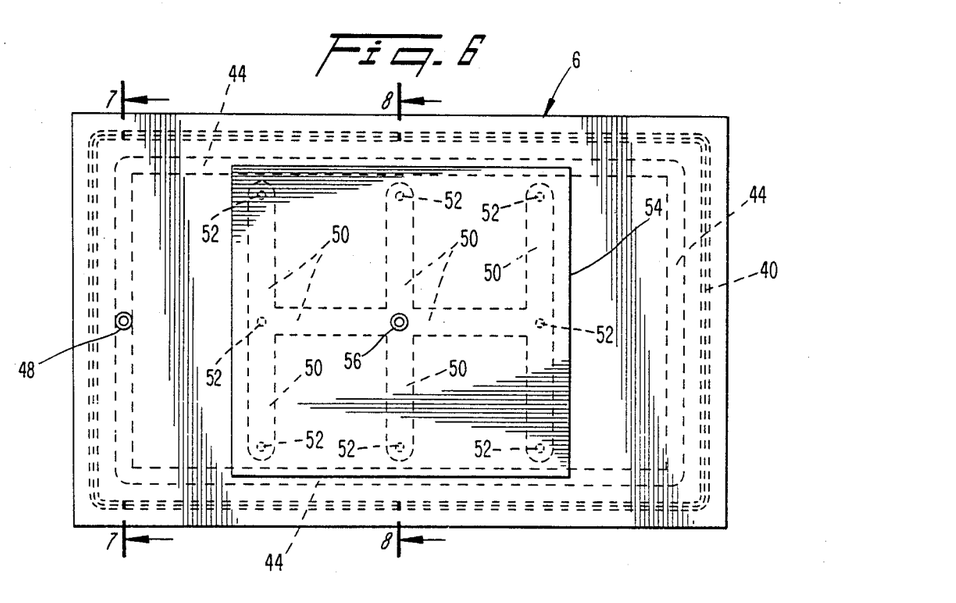
FIG. 6 is a top plan view of the lid for the cartridge.
Figure 7:
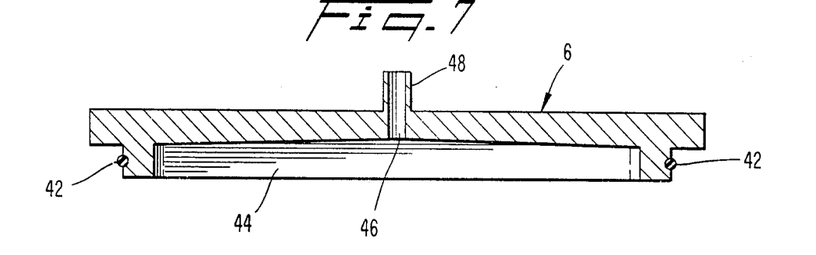
FIG. 7 is a cross-sectional view of the lid along the line 7—7 in FIG. 6.

As shown in FIG. 6, the lid 6 has a shoulder 40 which extends around the perimeter of the lid and engages the inside surface of the side walls 8 and the end walls 10. A sealing gasket 42 is retained within a groove in the shoulder 40. The gasket 42 prevents the leakage of fluid from the interior of the cartridge. A gas bubble channel 44 is formed in the interior of the lid 6 and extends along the end walls and side walls of the tray. The channel portion at the right side of FIG. 6 is more shallow than the groove at the left side of FIG. 6, and the grooves extending along the side walls 8 progressively increase in depth from the right end to the left end as viewed in FIG. 6. This arrangement of the grooves causes the gas bubbles to migrate progressively toward an outlet port 48 through the lid 6. The outlet port has a tube fitting 48 through which the gas bubbles can escape.

Figure 8:
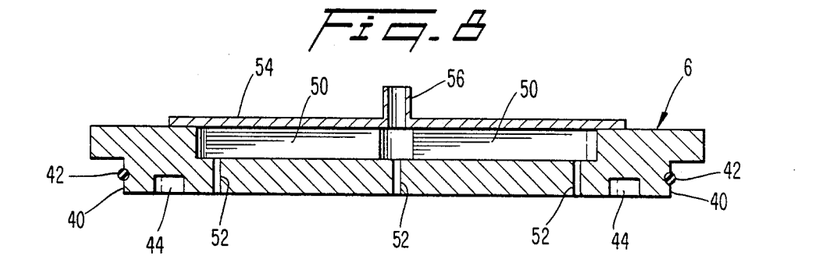
FIG. 8 is a cross-sectional view of the lid along the line 8—8 in FIG. 6.

The central portion of the lid 6 has a plurality of grooves 50 formed in the top side of the lid. As shown in FIGS. 6 and 8, ports 52 extend from the bottom of the grooves to the lower surface of the lid so that fluid can pass from the grooves 50 into the interior of the cartridge when the lid is in place. A cover plate 54 encloses the grooves 50 and a tube fitting 56 allows liquid to be conducted through the plate 54 into the interior of the grooves 50.

Figure 10:
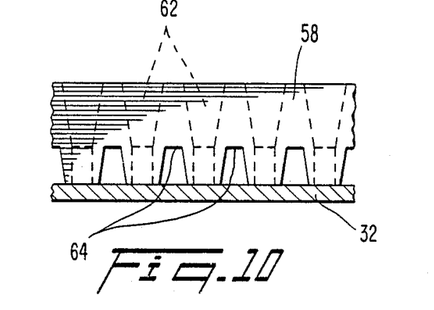
FIG. 10 is a front elevational view of the tray with the bridge installed as in FIG. 9.

In order to enable samples to be delivered into the wells formed in the gel layer 32, a bridge 58 is provided. The bridge aids in directing the operator to the correct well for sample filling thus making it easier to fill the well. The bridge is received in vertical slots 60 in each of the side walls 80 at a position that is aligned with the wells that are molded in the gel layer. A black strip may be positioned near the wells to aid in visualizing the wells during sample loading. The bridge 58 includes funnel-shaped passages 62 in a shape to receive the tip of a pipette for delivering the samples into the wells formed in the gel. As shown in FIG. 10, arches 64 are formed in the bridge between the passage 62 to allow fluid circulation between opposite sides of the bridge. If additional recirculation is necessary, the bridge can be removed prior to electrophoresis.

Figure 9:
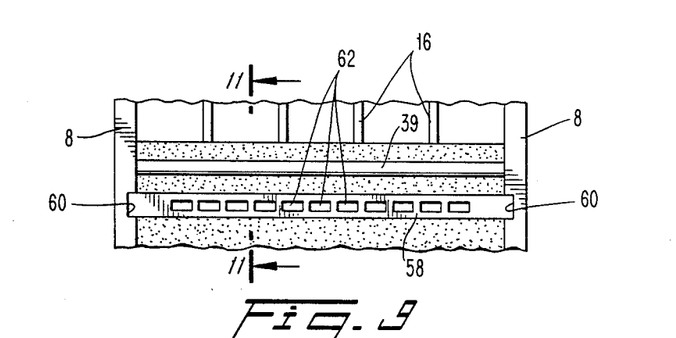
FIG. 9 is a detail plan view of the tray with the bridge installed.

In operation, a gel layer is formed in accordance with conventional practices of a proper size and shape to fit within the tray 4, so that the ends abut the ends of the webs 16 and the sides of the gel fit between the side walls 8 of the tray. Preferably, the gel is cast in a separate tray and has a series of wells molded in the gel layer adjacent on end. The gel 32 is then removed from the casting tray and placed on the porous plate 30, so that the gel 32 occupies the position shown in FIGS. 2, 9 and 11. The sloping top edge of each web 16 aids in guiding the gel into position in the tray 4. A source of electric potential is connected with the electrical connectors 28 and a system for circulating fluid is connected with the tubing fittings 22. An electrophoresis buffer is added to the tray to a depth that fully covers the electrodes 24 and the gel. The bridge 58 is installed in the slots 60 after the gel layer is positioned on the support surface 14. The samples are then delivered into the passages 62 from which they pass into the individual wells. The bridge remains in place when the lid 6 is applied. The electrophoresis buffer is recirculated through the passages 18 by the use of a conventional pump, to provide a fluid current passing over the gel. At the end of electrophoresis, the electrophoresis buffer is then withdrawn from the tray and a depurination buffer is pumped into the tray. After a predetermined period of time, the depurination buffer is then pumped out of the tray and a denaturation buffer is pumped into the tray. The gel tends to float in the denaturation buffer, and before the vacuum is applied, the membrane 31 is inserted manually into the space between the gel and the plate 30, as shown in FIGS. 5 and 11. The gel is then lightly pressed against the membrane and held in place by appropriate means, such as a band or tube 39, as shown in FIGS. 9 and 11. After a suitable elapse of time, the denaturization buffer is withdrawn through the vacuum fitting 38 at a relatively slow rate, which transfers the displaced samples from the gel onto the permeable membrane 31. As an alternative, water, or denaturation liquid may be sprayed onto the surface of the gel through the tube fitting 56 as the liquid is being withdrawn through the tube fitting 38. The lid 6 is then removed and the permeable membrane 31 may be removed from the tray for further processing. The membrane now contains the displaced samples in preparation for hybridization.

The cartridge of this invention has the important advantage that it allows electrophoresis and transfer to occur without having to remove the gel from the tray. At the completion of the operation, the nylon membrane bearing the samples can readily be removed for subsequent treatment.

The electrophoresis apparatus is designed to accommodate either a large number of analytical samples or milligram quantities of fragments for preparative runs. Typically, the number of samples which may be introduced into the cartridge may range from about 5 to 15. Generally, 10 samples plus two controls have been found to be suitable.

The tray 4 and the lid 6 must be compatible with standard electrophoresis and nucleic acid transfer reagents. Typical reagents include up to 3 molar (M) salts, acetic acid, 1 M hydrochloric acid and 0.5 M sodium hydroxide. Many polymers could be suitable for the present invention. Furthermore, in view of the direct current being used during electrophoresis, the tray 4 and lid 6 should not conduct electricity. The lid 6 is preferably plexiglass (acrylic) since a further advantage is obtained with the use of a clear cover since it would allow visual tracking of optional dyes during electrophoresis.

Using one buffer or solution throughout the foregoing procedure is more efficient and economical than using a different buffer or solution during each of the electrophoresis, depurination, denaturation and transfer stages. Alternatively, four separate solutions may be used in the practice of the present invention. For example, during electrophoresis any buffer well-known in the art is suitable such as any solution of a weak acid or base and its salts, such as acetates, borates, phosphates and phthalates, which behave as buffers. Typical compounds used in preparing buffers include acetic acid, phenylacetic acid, sodium acetate, ethylene diamine tetraacetic acid (EDTA), phosphoric acid, boric acid, hydrochloric acid, sodium hydroxide, sodium chloride and the like. During electrophoresis, a buffer comprised of 40 mM tris-acetate, pH 8, 12 mM sodium acetate and 2 mM EDTA, pH 8, is preferred.

During depurination, any solution which chemically assists in depurination or depyrimidination would be useful. These solutions are well-known in the art. A buffer comprised of 0.25 M hydrochloric acid can be used. It was discovered that during depurination, it is important to expose the lower surface of the gel as well as the top and side surfaces to the solution. For this reason, the membrane 31 is not inserted between the gel and the platform until just before applying the vacuum under the porous plate 30 to transfer the cells to the membrane.

During denaturation, any solution which assists in breaking the hydrogen bonds between the nucleic acid strands is suitable. These solutions are also well-known in the art. For example water and heat may provide satisfactory results, also formamide or any alkali such as sodium hydroxide or potassium hydroxide. In the present invention a solution of 0.5 M sodium hydroxide is preferred.

As the transfer solution, any solution which allows transfer and binding of the nucleic acid strands to the membrane would be suitable. These solutions are also well-known in the art. Advantageously, in the practice of the present invention the transfer solution is preferably 0.5 M sodium hydroxide, the same as the denaturation solution.

The time periods used in each of the above-described stages may vary over a wide range depending on the processing conditions. For instance, each of electrophoresis, denaturation and depurination may require from about 10 minutes to 5 hours. Useful techniques to decrease the amount of time required for processing include increasing the voltage, using larger ports, selecting the optimum thickness of the gel, different sizes of membranes and the support plate, and the like. A particular advantage of the present process is that the time required for electrophoresis is approximately 40–65% of the typical time required for electrophoresis using prior art apparatus and techniques. A significant time savings is offered by the present invention because of the circulation of fluids, i.e., buffers, through the electrophoresis transfer cartridge, thereby allowing a constant pH and temperature to be maintained during the process. In addition, the geometry of the cartridge results in concentrating the electric field within the gel which also speeds the process.

Furthermore, by maintaining a relatively frequent circulation of the buffer, a smaller volume of buffer is suitable in contrast to the buffer requirements of prior art electrophoresis processes.

The transfer step may require from about 10 minutes to two hours. Generally, about 60 minutes produces adequate results. This step also offers a considerable time savings over prior art transfer techniques. Capillary transfer, for instance, requires about 12 hours, squash blot transfer requires about 3 hours and standard electrotransfer requires about four hours.

A further advantage of the present invention is the time and labor savings that results since the apparatus is a cartridge. The decrease in the number of mechanical steps to be performed by a technician o operator assists in maintaining the accuracy of the procedure since a decrease in the number of necessary steps to be performed also minimizes error.

Other components are useful to achieve the objects of the present invention in addition to the above-described electrophoresis transfer cartridge. For instance, a microprocessor controller may be used to automate electrophoresis and DNA/RNA transfer. Such a controller would control the voltage and time for electrophoresis, the valves for reagents, the pumps to add and remove reagents and the vacuum system for DNA transfer. The electrophoresis transfer cartridge may be connected to a variety of standard laboratory equipment including peristaltic pumps.

The following example is intended to demonstrate one method that may be used to practice the present invention. The following is not intended to limit the invention in any way.

EXAMPLE

Electrophoresis Transfer Process

A 14 cm long $\times$ 11 cm wide $\times$ 0.65 cm deep 0.7% w/v agarose gel was placed and aligned in a polyvinyl chloride electrophoresis transfer tray having inside dimensions of 20 cm long $\times$ 11 cm wide $\times$ 2 cm deep. The gel rests on a liquid pervious platform or support plate made of porous polyethylene. Approximately 200 ml of an electrophoresis buffer comprised of 40 mM tris-acetate, 12 mM sodium acetate and 2 mM EDTA was added by hand.

Restriction enzyme digested human genomic DNA samples were loaded into the wells and a plexiglass top was placed over the polyvinyl chloride tray. The unit was then plugged into a power supply which was set at 90 volts. The power was turned on. Electrophoresis was allowed to continue for approximately ten minutes. Then the buffer was recirculated at a rate of approximately 25 ml/min for the duration of electrophoresis. Electrophoresis continued for approximately two hours. The power was turned off and the electrophoresis buffer was pumped out.

Approximately 200 ml of a depurination solution comprising 0.25 M hydrochloric acid was pumped into the polyvinyl chloride tray. The solution was allowed to stand for approximately 15 minutes and then the solution was pumped out. Next, approximately 200 ml of a denaturation solution was added to the polyvinyl chloride tray. A nylon membrane was inserted between the gel and the porous plate. A vacuum pump was turned on to withdraw fluid through the porous polyethylene plate at about 2 ml/min. This was continued for 60 minutes to allow the DNA to transfer from the gel to the nylon membrane below the gel. The unit was turned off.

Figure 12:
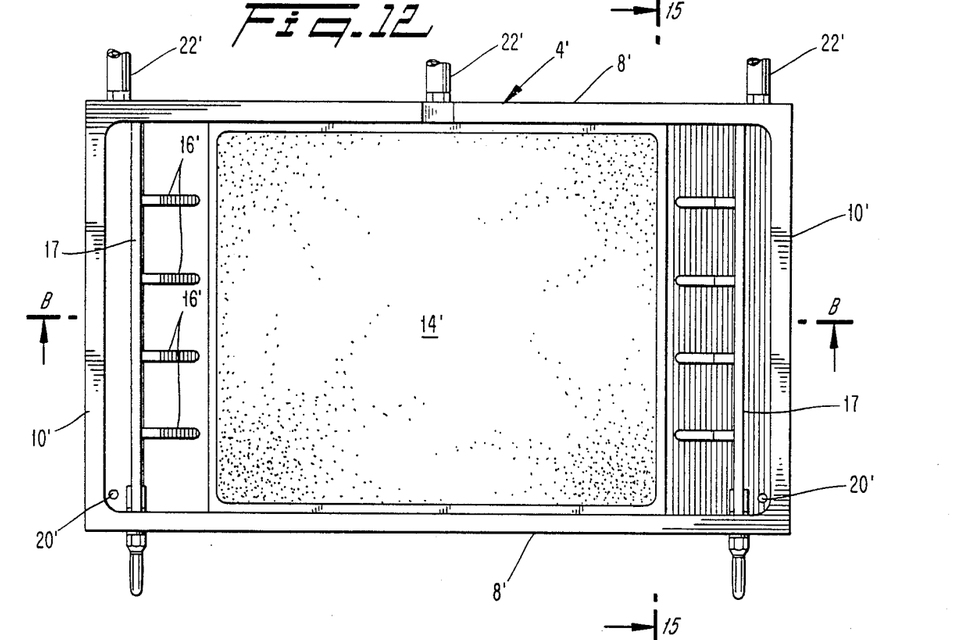
FIG. 12 is a top view of the tray as in FIG. 1 but showing the second preferred embodiment of the invention.
Figure 13:
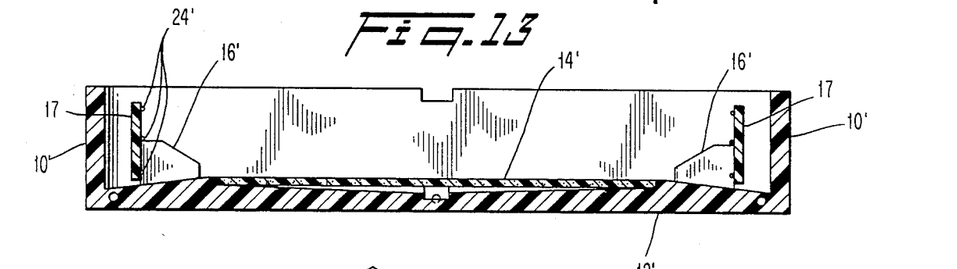
FIG. 13 is a cross-sectional view of the tray along the line 13—13 in FIG. 12.

A second preferred embodiment of the invention is illustrated in FIGS. 12-21. Instead of the plurality of ports 20 (FIG. 1) communicating with the passage 18 to allow the circulation of fluid into and out of the tray, the modified tray 4' as shown in FIG. 12, has a single port 20' at each end of the tray. Each port 20' has a diameter greater than that of each of the individual ports 20 of the first embodiment as shown in FIG. 1. A dam 17 is mounted at each end of the tray 4'. The dams 17 extend between the opposing side walls 8'. A plurality of webs 16' on the bottom wall 12' provide further support for the dam. Both of the dams have a transverse slot 21 (FIGS. 13 and 15) which extends substantially the full length of the dam.

The use of a single relatively large port 20' in combination with a dam 17 and slot 21 ensures uniform flow of liquid across the gel in electrophoretic systems where the liquid flow rate is typically small. The webs 16' also assist in avoiding lateral currents while the liquid is flowing. In the systems of FIG. 1, the liquid must be supplied at a relatively high pressure through the fitting 22 in order to obtain a uniform flow of liquid through each of the ports 20. At the low pressures associated with electrophoresis, therefore, there can result a higher flow rate of liquid across one portion of the gel than across another portion of the gel. In severe cases, this could affect the migration of the samples during electrophoresis, lead to overheating of the gel and disruption of the pH levels at those areas of the gel where the flow of buffer is insufficient.

The presence of a single larger port and a dam provides a uniform flow of material even with low pressure flows. The dam 17 forms a chamber 23 at both ends of the tray 4'. In these chambers, the turbulence or velocity pressures generated by the inflow and outflow of fluid is dissipated, and only a very minute head differential between the opposite sides of the dam 17 causes flow through the horizontal slot. The slot 21 can be either at the bottom of the chamber 23 as shown in FIG. 12, or part way up, but it must be entirely covered by the liquid surface. Turbulence in the end chambers is minimized by having the input and output supply systems as large as possible and by directing the input flow upward where the energy can be dissipated as waves on the surface. If the process fluid is suitable, open cell foam structures can be inserted in the chambers 23 to further dampen turbulence.

Another advantage of using a single larger port and a dam as opposed to a plurality of small ports to distribute a buffer liquid relates to the formation of air bubbles. More specifically, as buffer passes through the ports 20 into the tray, air bubbles can be carried along with the buffer. These air bubbles can collect until enough pressure builds up within the system so as to disrupt the flow of additional buffers into the tray. This problem may be so severe that it is necessary to incorporate specialized control systems within electrophoretic circulating equipment to effect removal of the entrained air and resumption of the buffer circulation. Due to changes in the physical chemistry of a fluid flowing through a single large port as opposed to a plurality of smaller ports, the present system eliminates bubble formation within the tray and thus concomitantly eliminates the need for special control equipment. The use of a larger buffer fluid port is also advantageous in that it enables particles carried by the circulating fluid to pass through easily.

Figure 16:
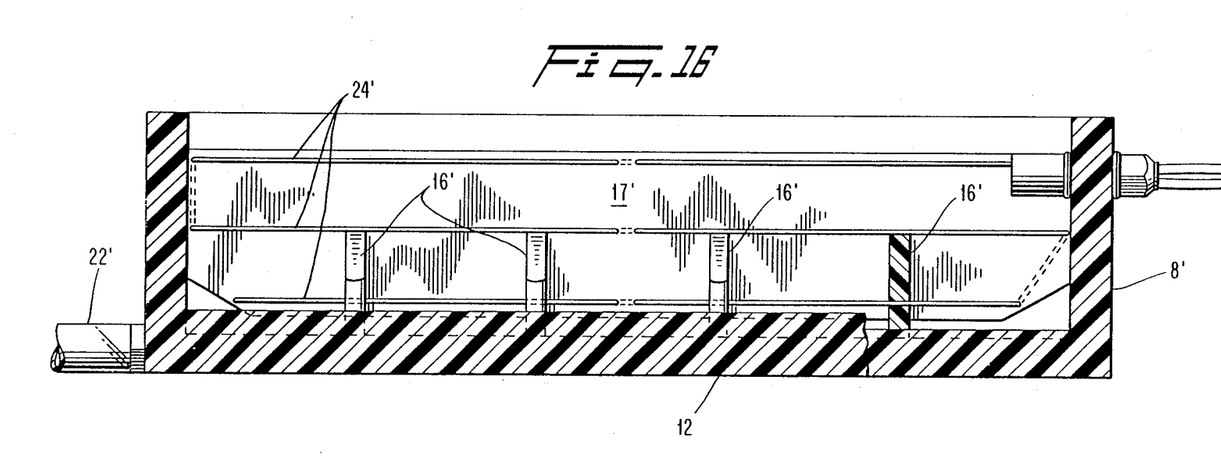
FIG. 16 is a cross-sectional view of the tray as in FIG. 15, but showing a modified form of the dam.

If it is desired to have other than uniform flow across the width of the gel, the slot can be modified to accomplish the desired objective and the adjustments are not unduly sensitive. For example, if it were desired to have a greater flow along the two outer edges in order to accomplish additional cooling, the slots could be widened at the edges as shown in FIG. 16.

The ports should be of size large enough to avoid bubble formation in the circulating fluid. It has been found that a hole size of 3 to 5 mm is satisfactory for this purpose. Although the port is shown near the side wall 8' of the device, it may be placed at any mechanically feasible location behind the dam 17. The horizontal slot formed by the dam and the bottom of the tray should be of a size large enough to permit passage of insoluble materials and small enough to generate uniform flow. For example, the slot may be between 1 and 5 mm in height.

Figure 14:
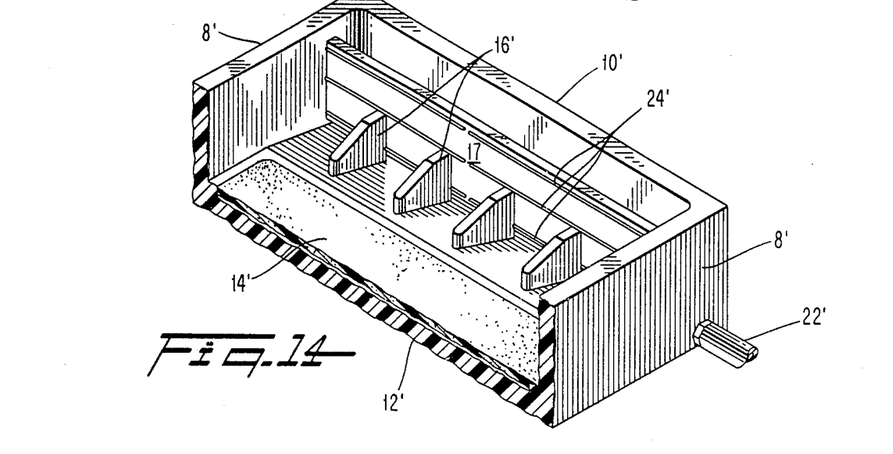
FIG. 14 is a perspective detail view of the tray of FIG. 12 showing the dam.
Figure 15:
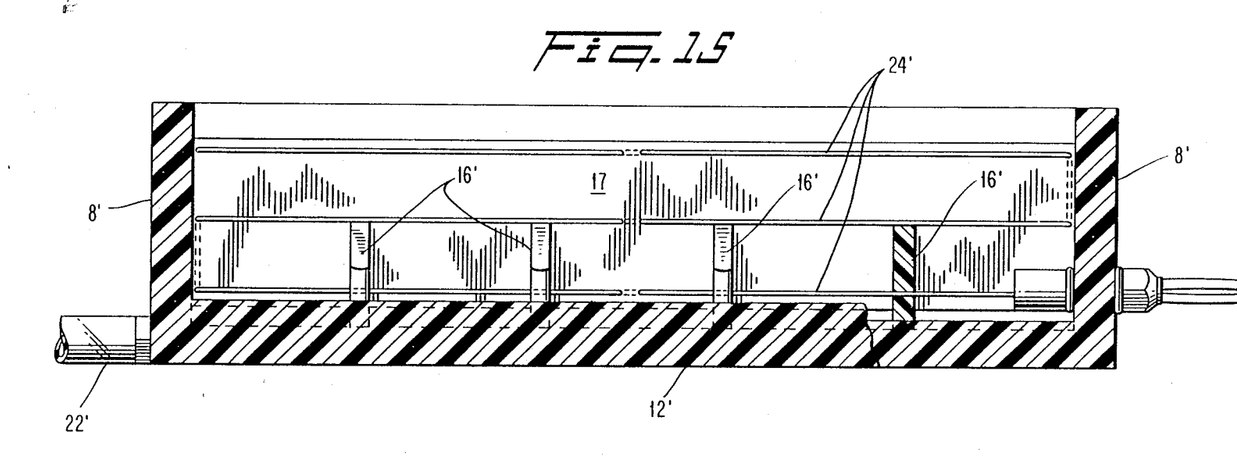
FIG. 15 is a cross-sectional view of the dam taken along the line 15—15 in FIG. 12.

As illustrated in FIGS. 14 and 15, three electrodes 24' are advantageously mounted on the surface of the dam 17 facing the gel. The mounting may be achieved simply by gluing the electrodes to the dam. Although a single electrode or two electrodes may be used, it has been found that three electrodes generate a more uniform electric field. More specifically, the thin wires typically employed in electrophoretic devices tend to vary in diameter thereby generating an electric field of varying intensity. By employing three such electrodes, variations in the diameter of each individual electrode tend to average out.

In operation, as decribed previously with respect to the first embodiment of this invention, the gel is placed in the tray 4' on the support surface 14' and an electrophoresis buffer is added to the tray to a depth that fully covers the electrodes 24' and the gel. The samples are then placed in the individual wells in the gel and circulation of the electrophresis buffer is started. The buffer flows into the chamber 23 at one end of the tray through the tubing 22' at a predetermined rate which corresponds approximately to the flow rate desired for the buffer. The buffer flows out of the chamber 23 through the slot 21 in the dam 17 in the direction toward the opposite end of the tray. The buffer enters the chamber 23 at the opposite end through the slot 21 and then flows out through the exit tubing 22'. This arrangement permits a very low flow rate, if desired. The remaining operation is essentially the same as previously described for the embodiment of FIG. 1, except that the table is withdrawn while sliding the gel onto the membrane 31 so that the gel occupies the position shown in FIG. 5.

Figure 20:
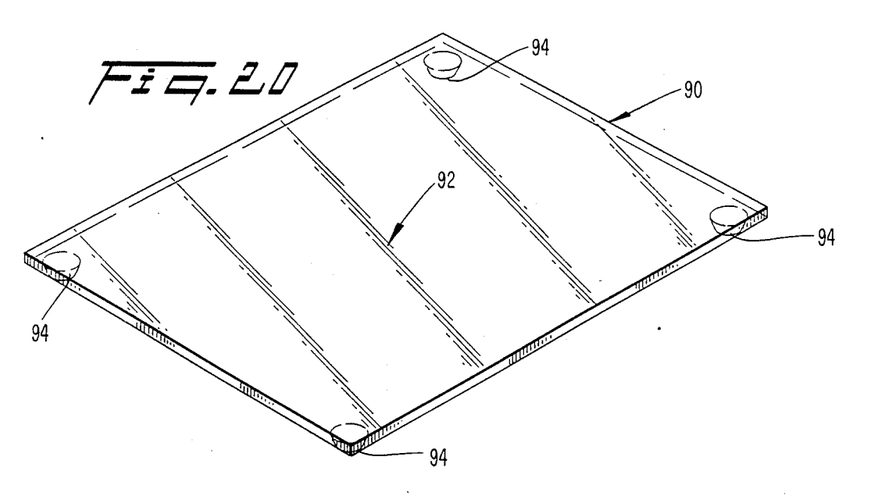
FIG. 20 is a perspective view of a table which can be placed on the support surface of the tray.

As illustrated in FIG. 20 the tray 4' may also be provided with a table 92 having four legs 94 for handling the gel and to improve the flow pattern of the buffer. The table should be constructed of a material which transmits ultraviolet light and should be of a size sufficient to hold the gel layer. The legs of the table are high enough so as to allow passage of buffer, including entrained particles, beneath the bottom surface of the table. The legs are also low enough so as to ensure that the gel layer resting on the table does not project above the surface of the buffer. Preferably, the table is 3 to 5 mm thick and is raised 2 to 4 mm above the support surface 14' of the tray.

When using the table, the agarose gel layer is placed on the top surface of the table and the table 92 is placed in the tray on the support surface 14'. By virtue of the table, buffer circulates both above and below the tray during electrophoresis thereby increasing the efficiency of the heat exchange between the buffer and the gel. Once electrophoresis is completed, the table with the gel can simply be lifted from the tray. Although such a step is not required according to the preferred embodiment, wherein the subsequent depurination and denaturation are carried out within the tray, the easily removable table does render it easier to process the gel in systems wherein the gel has to be removed from the tray. If vacuum transfer is to be performed in the tray, the table is withdrawn while sliding the gel onto the membrane 31 before vacuum transfer begins.

Figure 21:
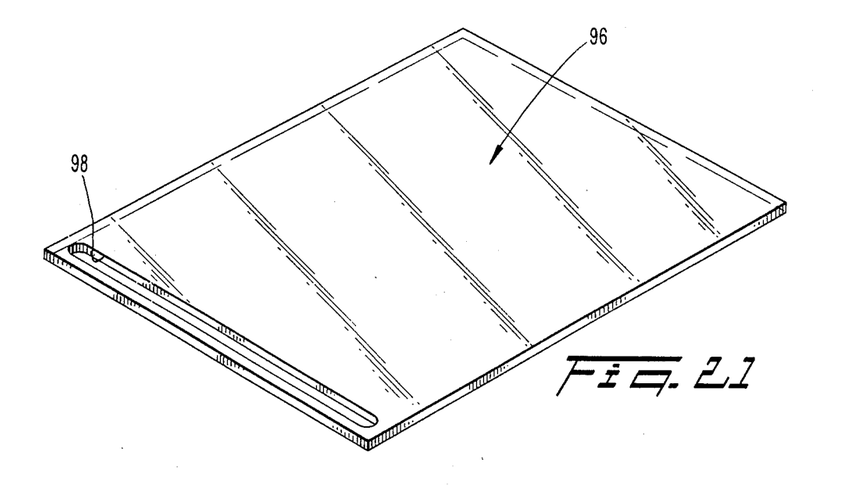
FIG. 21 is a perspective view of a heat sink plate which can be placed on the gel surface.

In order to further facilitate uniform heat distribution throughout the gel, there may also be provided a heat sink plate 96, illustrated in FIG. 21, made of a material such as plexiglass. Like the table 92, the heat sink plate 96 is dimensioned to correspond with the dimensions of the gel layer. The heat sink is advantageously 3 to 5 mm thick and is provided with a slot 98 along one of the ends thereof to correspond to the wells in the gel. In operation, the heat sink plate 96 is placed on the gel for the electrophoresis step. Because the gel tends to float during electrophoresis, the heat sink plate 96 does not interfere with the flow of buffer above the gel surface.

Figure 17:
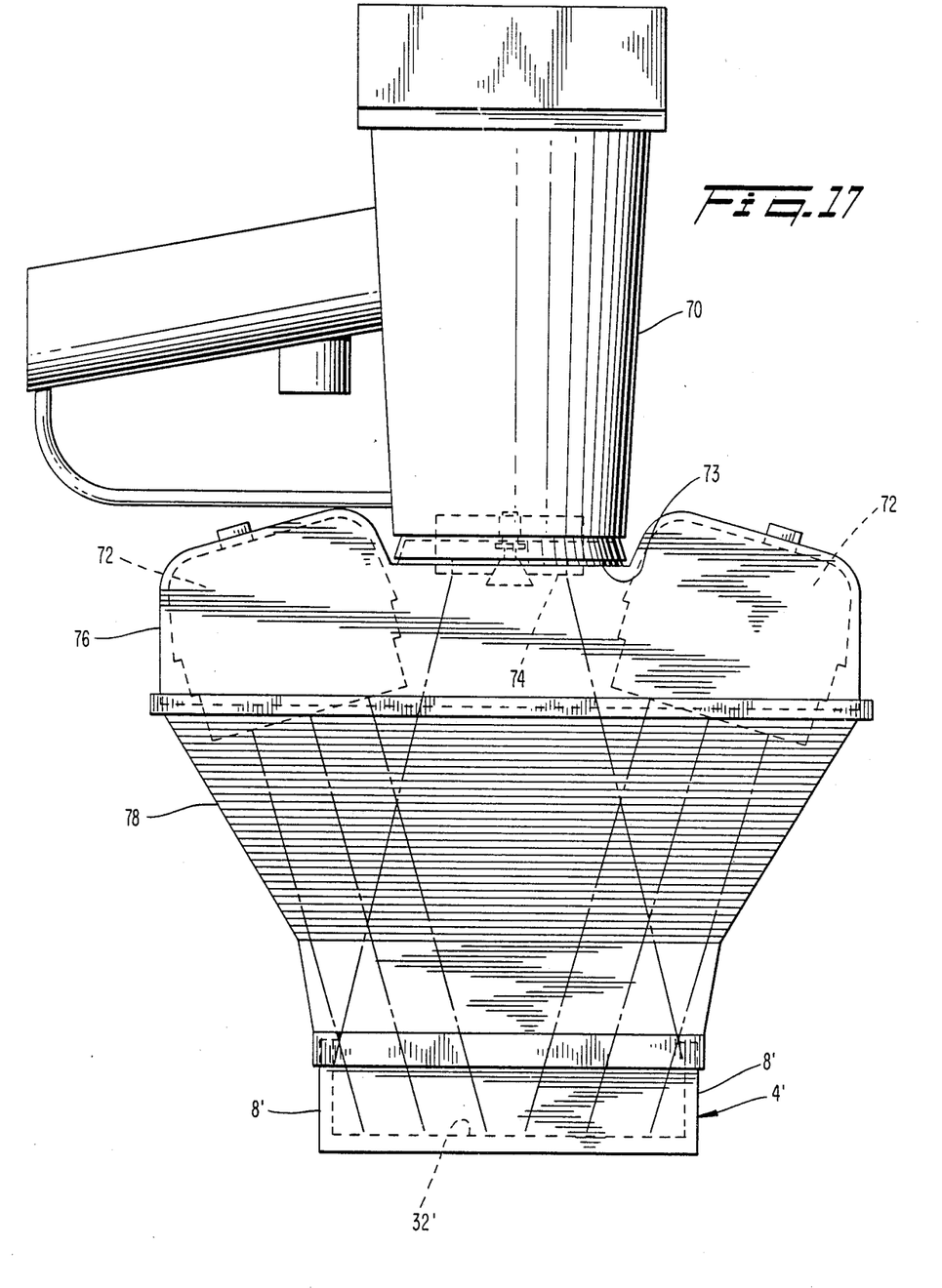
FIG. 17 is a front elevational view of the tray and hood which supports a camera and ultraviolet light sources.
Figure 18:
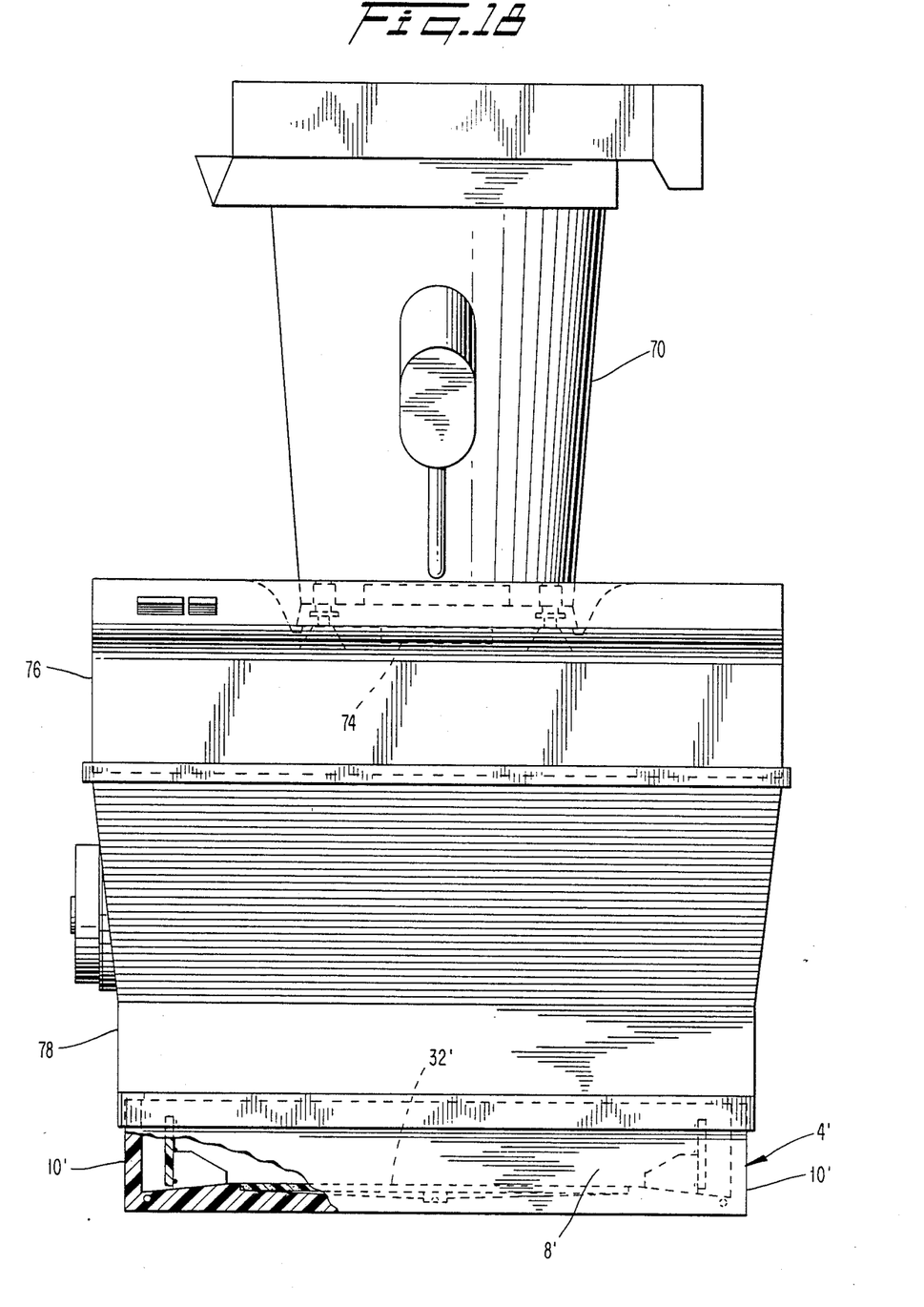
FIG. 18 is a side elevational view of the tray and hood as in FIG. 17.

According to the second preferred embodiment, an arrangement is also provided for exposing the sample on the gel to ultraviolet light. Ultraviolet light can be used in combination with ethidium bromide to both nick the DNA strand and to facilitate photography of the fluorescent DNA bonds. The apparatus for exposing the tray to ultraviolet light is illustrated at FIGS. 17 and 18. The apparatus includes a camera 70 having a lens 74. The front of the camera 73 including the lens 74 is connected to a two-piece opaque housing including a top member 76 and a bottom member 78. The top member 76 houses a pair of ultraviolet lamps 72 on either side of the lens 74. The lamps 74 are at an angle relative to the front of the camera 73 so that ultraviolet rays will be directed onto the gel 32'. The bottom member 78 connects the top member 76 with the tray at the opposing side walls 8' and end walls 10' of the tray 4'.

Figure 19:
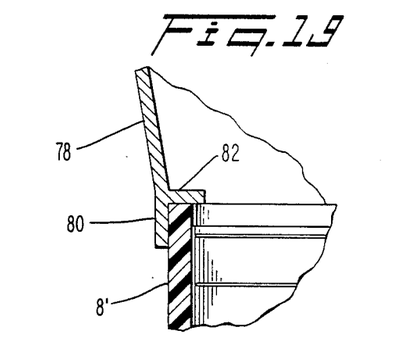
FIG. 19 is a cross-sectional view of the connection between the bottom member of the opaque chamber and the side of the tray taken along the line 19—19 in FIG. 18.

As illustrated in FIG. 19, a light-tight connection between the bottom member 78 and the end wall of the tray 8' is achieved by a continuous flange 82 resting on and overlaping the top edge of the side walls 8' and end walls 10' and by a continuous collar 80 extending along the upper portion of the outside surface of the tray 4'. The flange 82 and the collar 80 fit tightly on the tray, so that light cannot enter the interior of the member 78.

The apparatus for exposing the tray to ultraviolet light can be used in conjunction with ethidium bromide as an alternative to hydrochloric acid for depurination.

More specifically, an electrophoresis buffer containing 0.5 to 1.0 g/ml ethidium bromide or other intercalating dyes which generate strand breaking energy when excited by ultraviolet light may be used. The tray is then exposed to ultraviolet light so as to effect nicking of the DNA strand. Typically, 5 to 15 minutes of exposure to ultraviolet light are required to effect the desired nicking. As is known to persons skilled in the art, the locations of the nicks using the ethidium bromide/ultraviolet light system are somewhat different than the locations of the nicks using HCl. The end result is the same however namely, nicking of the DNA strands so as to enable, after denaturation, transfer of the material.

While this invention has been illustrated and described in accordance with a preferred embodiment, it is recognized that variations and changes may be made therein without departing from the invention as set forth in the claims.

What is claimed is:

1. Apparatus for conducting electrophoresis and subsequent transfer, comprising:
   a tray having opposite side walls, opposite end walls and a bottom wall;
   platform means in said tray including a top surface for supporting a gel;
   electrode means for applying an electric field in said tray between said end walls, said platform means being between said electrode means;
   dam means in said tray extending along said opposite end walls, said dam means being spaced from said end walls and having a transverse slot adjacent said bottom wall and substantially aligned with said top surface of said platform means; and
   conduit means for transferring liquid into and out of said tray, said conduit means including a port between each end wall and the adjacent dam means.

2. The apparatus of claim 1 further including a table adapted to fit over said platform means.

3. The apparatus of claim 2 wherein said table is constructed of a material which transmits ultraviolet light.

4. The apparatus of claim 1 further including a heat sink plate having substantially the same shape as said platform means and adapted to be superimposed on a gel that is supported on said platform means.

5. The apparatus of claim 4 wherein said heat sink plate is provided with a slot corresponding to sample wells in an underlying gel.

6. The apparatus of claim 1 further including:
   (i) a housing including an ultraviolet light source;
   (ii) a light-tight means for connecting said housing to said tray.

7. The apparatus of claim 6 wherein said housing further includes a camera.

8. The apparatus of claim 7 wherein said camera is positioned adjacent to the ultraviolet light source and said camera is aligned with said platform means.

9. The apparatus of claim 6 wherein said means for connecting said housing to said tray includes (i) a continuous flange resting on and overlapping the top edge of the side wall and end wall of said tray and (ii) a continuous collar extending along the upper portion of the outside surface of the tray.

10. The apparatus of claim 1 wherein said tray includes a plurality of webs between said dam means and said platform means.

11. The apparatus of claim 10 wherein said webs extend between said dam means and said bottom wall and are spaced apart along said dam means.

12. The apparatus of claim 11 wherein said slot is of a height large enough to permit passage of insoluble materials and small enough to generate uniform flow.

13. The apparatus of claim 1 wherein said electrode means is mounted on said dam means.

14. The apparatus of claim 13 wherein said electrode means includes three wires mounted at different heights across said dam means.

15. The apparatus of claim 1 wherein said port is of a size great enough to prevent formation of bubbles in said liquid.

16. Apparatus for conducting electrophoresis according to claim 4 further comprising:
    lid means for covering said tray;
    a plate separate from said support surface and adapted to be superimposed over said support surface, whereby when a gel layer is placed on said support surface and said plate is applied over said gel layer, said plate serves as a heat sink during electrophoresis; said lid means being spaced from said plate when said plate is applied over said gel layer.

17. Apparatus for conducting electrophoresis comprising:
    a tray having opposite side walls, opposite end walls and a bottom wall, said tray including a support surface above said bottom wall and between said opposite side walls and opposite end walls of said tray;
    electrode means for applying an electric field in said tray across said support surface; and
    a separate table on the support surface of said tray, said table having a top and bottom surface, said table including spacer means extending from the support surface of the tray to the bottom surface of said table for spacing said bottom surface above said support surface of said tray and to provide a space between the bottom surface of said table and the top surface of said tray, said top surface being adapted to support a gel layer during electrophoresis, whereby when a buffer is supplied to the tray, the table facilities heat exchange between the buffer and the gel.

18. The apparatus according to claim 17 wherein said table is separate from said support surface, whereby the gel layer may be placed on the table outside the tray and the table with the gel layer may then be placed on the support surface.

19. The apparatus according to claim 17 including a plate in said tray superimposed over said table, whereby when a gel layer is placed on the tray, the plate covers the gel layer to resist the tendency of the gel layer to float in a buffer during electrophoresis and to serve as a heat sink.

20. The apparatus according to claim 19 wherein said plate is formed of plexiglass.

21. The apparatus according to claim 19 wherein said plate has a transverse slot.

22. The apparatus of claim 17 further including means for delivering an electrophoretic fluid above and below said table.

23. The apparatus of claim 17 wherein said table includes a substantially flat top.

24. The apparatus of claim 17 wherein said table has opposite ends, said top and bottom surface of said table are substantially flat and wherein said spacer means are legs at the opposite ends of said table.

25. Apparatus for conducting electrophoresis comprising:
    a tray having opposite side walls, opposite end walls and a bottom wall;
    platform means in said tray for supporting a gel;
    electrode means for applying an electric field in said tray across said support surface;
    liquid reservoir means for containing buffer liquid in said tray;
    a housing having an opening corresponding to the width and length of said side walls and end walls of said tray, said opening including means for forming a light-tight connection between said side walls and said end walls;
    an ultraviolet light source in said housing; and means for mounting a camera in said housing.

26. The apparatus according to claim 25 including a transparent plate separate from said platform means; said plate being superimposed on said platform means with a gel layer between said plate and said platform means.

27. The apparatus according to claim 26 wherein said platform means includes a table having a top surface and a bottom surface, said gel layer being positioned between said top surface and said plate while said electroporesis is being conducted.

28. The apparatus according to claim 25 wherein said ultraviolet light source includes a pair of ultraviolet lamps on opposite sides of the means for mounting a camera.

* * * * *